United States Patent [19]

Conine et al.

[11] Patent Number: 5,114,948
[45] Date of Patent: May 19, 1992

[54] STABILIZED PERGOLIDE COMPOSITIONS

[75] Inventors: James W. Conine, Indianapolis; Denis L. Sparks, Greenwood; Julian L. Stowers, Indianapolis, all of Ind.

[73] Assignee: Eli Lilly and Company, Indianapolis, Ind.

[21] Appl. No.: 424,018

[22] Filed: Oct. 19, 1989

[51] Int. Cl.$^5$ .............................................. A61K 31/44
[52] U.S. Cl. .................................... 514/288; 514/973
[58] Field of Search ................... 424/80; 514/288, 973

[56] References Cited

U.S. PATENT DOCUMENTS 4,166,182  8/1979  Kornfeld et al. ..................... 546/67
4,180,582 12/1979  Kornfeld et al. ..................... 424/261
4,797,405  1/1989  Conine et al. ....................... 514/288

FOREIGN PATENT DOCUMENTS 64-63519  3/1989  Japan.
64-63520  3/1989  Japan.

Primary Examiner—Frederick E. Waddell
Assistant Examiner—Zohreh A. Fay
Attorney, Agent, or Firm—Robert A. Conrad; Leroy Whitaker

[57] ABSTRACT

Pharmaceutical compositions containing pergolide or a salt thereof stabilized to oxidation by incorporation therewith of a stabilizing agent selected from methionine, cysteine, and cysteine hydrochloride.

17 Claims, No Drawings

STABILIZED PERGOLIDE COMPOSITIONS

BACKGROUND OF THE INVENTION

Pergolide is an ergoline derivative which exhibits potent dopaminergic agonist activity and also decreases plasma prolactin concentrations. The compound is therefore useful in treating physiological manifestations associated with hyperprolactinemia. Chemically, pergolide is D-6-n-propyl-8β-methylmercaptomethylergoline. Pergolide mesylate is sold commercially as PERMAX® for adjunctive treatment to levodopa/carbidopa in the management of the signs and symptoms of Parkinson's disease.

Pergolide is known to decompose upon exposure to light (apparently to a sulfoxide species) thus making it necessary to handle the compound and store the ultimate dosage form in light-controlled environments so as to avoid a demonstrable drop in potency of the therapeutic agent. In order to retard this drop in potency, certain stabilizing agents have been incorporated into pharmaceutical compositions containing pergolide which surprisingly reduce the decomposition of this compound when exposed to light; see U.S. Pat. No. 4,797,405.

We have now discovered that pergolide is converted into its sulfoxide during handling in the manufacturing process. This is especially true for preparing tablets with a large excipient to drug ratio —e.g., those containing approximately 50 mcg of pergolide in a tablet of about 300 mg total weight. Under normal manufacturing process, sulfoxide levels of 6–9 percent have been seen immediately after compression of the tablet. Even with special handling, sulfoxide levels are typically 3 percent immediately after the manufacturing process.

We have now discovered that the addition of methionine, cysteine, or cysteine hydrochloride as part of the pharmaceutical composition of pergolide tablets will greatly reduce the formation of the sulfoxide during the manufacturing process.

SUMMARY OF THE INVENTION

The present invention is directed to a pharmaceutical composition of pergolide or a salt thereof stabilized to prevent formation of pergolide sulfoxide during the manufacturing process. Said composition comprises a therapeutically effective amount of pergolide or a salt thereof, a stabilizing agent selected from methionine, cysteine, and cysteine hydrochloride in an amount sufficient to retard the formation of pergolide sulfoxide, and pharmaceutically acceptable excipients.

Also disclosed is a method of stabilizing a pharmaceutical composition of pergolide or a salt thereof to oxidation during the manufacturing process. The method comprises incorporating into said pharmaceutical composition, in addition to a therapeutically effective amount of perqolide or a salt thereof and pharmaceutically acceptable excipients, a stablizing agent selected from methionine, cysteine, and cysteine hydrochloride in an amount sufficient to effect stablization to oxidation.

DETAILED DESCRIPTION OF THE INVENTION

Pergolide (i.e., D-6-n-propyl-8β-methylmercaptomethylergoline) may be prepared as described in U.S. Pat. No. 4,166,182, which is incorporated herein by reference. Briefly, methyl dihydrolysergate is treated with cyanogen bromide in an inert solvent such as chloroform, methylene dichloride, toluene, DMF and the like to form D-6-cyano-8β-methoxycarbonyl ergoline. The cyanide group is then readily removed as by zinc dust in acetic acid forming a secondary amine function at N-6 which can then be re-alkylated with, for example, N-propyl iodide in an inert, preferably polar solvent such as dimethylformamide or nitromethane at temperatures in the range of 20°–50° centigrade (C.). The ester function at C-8 is then reduced by treatment with, for example, sodium borohydride in dioxane to form D-6-n-propyl-8β-hydroxymethylergoline which is then reesterified by treatment with methanesulfonyl chloride in pyridine to form D-6-n-propyl-8β-mesyloxymethyl ergoline. The mesyloxy derivative is then treated with methylmercaptan in dimethyl acetate to render D-6-n-propyl-8β-methylmercaptomethylergoline (pergolide).

The above-noted U.S. patent discloses that various salts of pergolide may be prepared including acid addition salts of inorganic acids such as hydrochloric, nitric, phosphoric and sulfuric acids as well as salts derived from nontoxic organic acids. Such salts thus include sulfate, nitrate, phosphate, acetate, propionate, caprylate, oxalate, malonate, phenylacetate, citrate, lactate, malate, tartrate, maleate, methanesulfonate, toluenesulfonate and the like. For purposes of the present invention, a preferred salt is the methanesulfonate salt, prepared by treating D-6-n-propyl-8β-methylmercaptomethylergoline with methanesulfonic acid to yield D-6-n-propyl-8β-methylmercaptomethylergoline methanesulfonate or simply pergolide mesylate.

It has been found that pharmaceutical compositions of pergolide or a salt thereof may be stabilized to oxidation during the manufacturing process by the addition to said composition of a stabilizing agent selected from methionine, cysteine, and cysteine hydrochloride. These three compounds are commercially available amino acids each of which can exist as the racemate or pure D- or L-forms. Preferably, the stabilizing agent used in the present invention is L-methionine.

For purposes of the present invention, one or more (preferably one) of the stabilizing agents disclosed herein is present in the pharmaceutical composition in an amount sufficient to effect stabilization to oxidation of said composition. For L-methionine this amount may vary from 0.1 to 2 percent by weight of the total composition and is preferably 0.2 to 1.0 percent by weight of the total composition. For cysteine and cysteine hydrochloride, this amount may vary from 0.05 to 1.0 percent by weight of the total composition and is preferably 0.15 to 0.3 percent by weight of the total composition. Generally, the amount of these stabilizing agents will be about 10–20 times the amount of pergolide present in the formulation. The precise amount of stabilizing agent to be used in a particular composition will, of course, vary depending upon the ultimate size of the dosage form, the specific dosage form chosen, the amount of pergolide present in the dosage form, and the like. Suffice it to say that the pharmaceutical composition will contain the stabilizing agent in an amount sufficient to effect stabilization to oxidation of said composition. That is, the composition will be less readily decomposed when one of the stabilizing agents disclosed herein is incorporated with said composition. This effect is particularly useful in tablets of smaller size and pergolide content, e.g., tablets weighing approximately 300 mg containing approximately 73 mcg of pergolide mesylate, where the tablets have a relatively low drug concentration, i.e., the tablets have a large excipient to drug ratio.

The addition of such stabilizing agents to prevent pergolide sulfoxide formation during the manufacturing process can be employed separately or preferably used in combination with the light stabilizing agents as provided by U.S. Pat. No. 4,797,405. Thus, in addition to the amounts of methionine, cysteine, or cysteine hydrochloride as described above, the preferred formulations are those which additionally include polyvinylpyrrolidone, α-tocopherol succinate, or propyl gallate in the same amounts as provided by the U.S. Pat. No. 4,797,405. A particularly preferred embodiment, therefore, is that wherein approximately 70–75 mcg of a salt of pergolide, especially pergolide mesylate, which is equivalent to approximately 50 mcg of pergolide base, is combined with about 1 mg of L-methionine and 4 mg of polyvinylpyrrolidone. Together with other excipients, such as lactose, sodium carboxymethyl cellulose, iron oxide yellow, and magnesium stearate, the mixture is compressed to provide tablets weighing approximately 300 mg. Thus, a preferred tablet formulation comprises approximately 0.02-0.03% pergolide mesylate, 0.2-0.4% L-methionine, and 1-2% polyvinylpyrrolidone.

The pharmaceutical compositions which are stabilized to oxidation contain a therapeutically effective amount of pergolide or a salt thereof. As used herein, the term "therapeutically effective" refers to that amount of pergolide or a salt thereof sufficient to deliver, in single or divided doses, 0.01 to 6 milligrams (mg) of pergolide per day to the subject being administered. In a preferred embodiment, when pergolide mesylate is the pergolide salt in the composition, it is present in an amount sufficient to deliver, in single or divided doses, 0.05 to 3 mg of pergolide per day to the subject being administered. The skilled artisan will readily recognize that the therapeutically effective amount may vary widely particularly where the route of administration and the particular salt or free base being employed are considerations. Of course, other factors such as the weight or age of the subject being treated as well as the time, frequency and specific pharmaceutical formulation employed in the administration are to be considered in determining the therapeutically effective amount in a given situation. This amount may be readily ascertained in a particular instance by the skilled artisan utilizing conventional dose titration techniques.

The pharmaceutical compositions of pergolide or a salt thereof stabilized to oxidation are preferably compositions for oral administration. Such compositions include any of the conventional solid or liquid dosage forms such as, for example, tablets, capsules, powders, suspensions, and the like including any sustained release preparations thereof. In addition to pergolide (or a salt thereof) and stabilizing agent, the pharmaceutical compositions of the present invention for oral administration utilize pharmaceutically acceptable excipients including, but not limited to, diluents, carriers, lubricants and the like such as glucose, lactose, sucrose, corn and potato starch, microcrystalline cellulose, sodium carboxymethylcellulose, ethyl cellulose, cellulose acetate, powdered gum tragacanth, gelatin, alginic acid, agar, stearic acid, sodium, calcium and magnesium stearates, sodium lauryl sulfate, sodium citrate, calcium carbonate, dicalcium phosphate among others; as well as various buffering agents, surfactants, emulsifiers, dispersing agents, flavoring agents and the like.

Preparation of the pharmaceutical compositions disclosed herein are readily achieved by one skilled in the art. Further, the skilled artisan will appreciate that the ultimate pharmaceutical composition may be provided in multiple or discrete, unit dose fashion with the latter being preferred. In addition to the information provided herein pertinent to the preparation of the pharmaceutical compositions of the invention, further reference may be obtained from standard treatises such as *Remington's Pharmaceutical Sciences*, Seventeenth Edition, Mack Publishing Co., Easton, Pa. (1985) which is incorporated herein by reference.

The invention will now be illustrated by the following examples which shall not be construed as a limitation thereon.

Tablets weighing approximately 300 mg and containing approximately 50 mcg of pergolide (as the active ingredient) were prepared generally as follows. For each tablet, 288.05 mg of lactose, 6.0 mg of carboxymethylcellulose sodium crosslinked, and 0.13 mg of iron oxide yellow were added to a mixer and blended. A solution of 0.03 ml of methanol, 0.073 mg of pergolide mesylate (corresponding to approximately 0.050 mg of pergolide), 0.025 ml of water, and 4.0 mg of polyvinylpyrrolidone was prepared. The dry mixture was then granulated with the hydroalcoholic solution and the resulting granulation was air dried, screened, blended with 1.75 mg of magnesium stearate, and compressed into tablets weighing approximately 300 mg each. This general procedure was used for tablets A, C, D, and E below. In the case of tablets C, D, and E, the appropriate amount of lactose was replaced with 1 mg of L-methionine, 0.5 mg of cysteine, and 0.5 mg of cysteine hydrochloride, respectively.

In tablets B, a modified manufacturing process was employed using the same general procedure as described above. 90% of the hydroalcoholic solution without the pergolide mesylate was granulated with 90% of the dry mixture. The resulting "placebo" granulation was then air-dried, sieved, and blended with 90% of the magnesium stearate. The remaining 10% of the dry mixture was then separately granulated with the remaining 10% of the hydroalcoholic solution containing the entire amount of pergolide mesylate. This "active" granulation was air-dried, sieved, and blended with the remaining 10% of the magnesium stearate. The "placebo" and "active" granulations were then added together, mixed, and the resulting mixture compressed into tablets weighing approximately 300 mg each. Although as demonstrated below this modified manufacturing process resulted in less formation of pergolide sulfoxide, the resulting tablets also were less homogeneous than tablets prepared by the original process.

Following preparation of the respective formulations, the tablets were assayed for their pergolide sulfoxide content. In the case of tablets A, B, D, and E, this was generally accomplished within two weeks of tablet formation. In the case of tablet C, the analysis was performed 6–8 weeks following tablet formation. In each case, the bulk pergolide mesylate employed to make the respective tablets contained no more than 0.1% sulfoxide.

Table 1 which follows reports the percent pergolide sulfoxide determined for each of the respective tablets. Three different lots each of tablets A, B, and C were made and evaluated.

TABLE 1

| Tablet | Lot | % Pergolide Sulfoxide* |
|---|---|---|
| A[1] | 1 | 6.9 |
|  | 2 | 9.1 |
|  | 3 | 7.5 |
| B[2] | 1 | 2.17 |
|  | 2 | 2.33 |
|  | 3 | 1.89 |
| C[1,a] | 1 | 0.71** |
|  | 2 | 0.65** |
|  | 3 | 0.83** |
| D[1,b] | 1 | 0.37 |
| E[1,c] | 1 | 0.52 |

[1] prepared by general process described above
[2] prepared by modified placebo/active formulation combination process described above
[a] contained 1 mg L-methionine per tablet
[b] contained 0.5 mg cysteine per tablet
[c] contained 0.5 mg cysteine hydrochloride per tablet
*except as noted, determination of pergolide sulfoxide was determined within 2 weeks of tablet formation
**Assayed 6-8 weeks after tablet formation

We claim:

1. A pharmaceutical composition of pergolide or a salt thereof stabilized to oxidation comprising a therapeutically effective amount of pergolide or a salt thereof, a stabilizing agent selected from methionine, cysteine, and cysteine hydrochloride in an amount sufficient to effect stabilization to oxidation, and pharmaceutically acceptable excipients.

2. A pharmaceutical composition of claim 1 wherein the pergolide is present as pergolide mesylate.

3. A pharmaceutical composition of claim 2 wherein the stabilizing agent is L-methionine.

4. A pharmaceutical composition of claim 3 wherein the L-methionine is present in said composition in an amount of from 0.1 to 2 percent by weight of the total composition.

5. A pharmaceutical composition of claim 4 wherein the L-methionine is present in said composition in an amount of from 0.2 to 1.0 percent by weight of the total composition.

6. A pharmaceutical composition of claim 5 which is a tablet weighing approximately 300 mg containing approximately 73 mcg of pergolide mesylate and approximately 1 mg of L-methionine.

7. A composition of claim 1 which additionally contains a compound selected from polyvinylpyrrolidone, propyl gallate, and α-tocopherol in an amount sufficient to effect stabilization to decomposition by light.

8. A composition according to claim 7 wherein the light stability agent is polyvinylpyrrolidone.

9. A composition according to claim 8 wherein the oxidation stabilizing agent is L-methionine.

10. A composition according to claim 9 wherein pergolide is present as the mesylate salt.

11. A composition according to claim 10 which is about 0.02–0.03% pergolide mesylate, about 0.2–0.4% L-methionine, and about 1–2% polyvinylpyrrolidone.

12. A composition according to claim 11 which is a tablet weighing approximately 300 mg containing approximately 73 mcg of pergolide mesylate, approximately 1 mg of L-methionine, and approximately 4 mg of polyvinylpyrrolidone.

13. A method of stabilizing a pharmaceutical composition of pergolide or a salt thereof to decomposition by oxidation comprising incorporating into said pharmaceutical composition, in addition to a therapeutically effective amount of said pergolide or a salt thereof and pharmaceutically acceptable excipients, a stabilizing agent selected from methionine, cysteine and cysteine hydrochloride in an amount sufficient to effect stabilization to decomposition by oxidation.

14. The method of claim 13 wherein the pergolide is present as pergolide mesylate.

15. The method of claim 14 wherein the stabilizing agent is L-methionine.

16. The method of claim 15 wherein the L-methionine is present in an amount of from 0.1 to 2 percent by weight of the total composition.

17. The method of claim 16 wherein the L-methionine is present in an amount of from 0.2 to 1.0 percent by weight of the total composition.

* * * * *